United States Patent [19]

Porubcan et al.

[11] 4,115,199

[45] Sep. 19, 1978

[54] PREPARATION OF CULTURE CONCENTRATES FOR DIRECT VAT SET CHEESE PRODUCTION

[75] Inventors: Randolph S. Porubcan, West Allis; Robert L. Sellars, Waukesha, both of Wis.

[73] Assignee: Chr. Hansen's Laboratory, Inc., Milwaukee, Wis.

[21] Appl. No.: 793,483

[22] Filed: May 4, 1977

[51] Int. Cl.$^2$ .......................... C12K 3/00; C12B 1/26; A23C 19/02; A23C 23/00
[52] U.S. Cl. ........................................ 195/96; 426/34; 426/36; 426/43; 426/491
[58] Field of Search ..................... 195/96; 426/34, 43, 426/61, 491, 36

[56] References Cited

U.S. PATENT DOCUMENTS

| Re. 28,276 | 12/1974 | Farr | 195/96 |
|---|---|---|---|
| 3,041,248 | 6/1962 | Hargrove | 195/96 X |
| 3,968,256 | 7/1976 | Sing | 426/43 X |

*Primary Examiner*—David M. Naff
*Attorney, Agent, or Firm*—Tilton, Fallon, Lungmus & Chestnut

[57] ABSTRACT

Concentrated bacterial cultures for direct vat inoculation of milk batches are prepared by centrifugation of the fermented culture in the presence of dissolved polyphosphate. Improved cell recovery and higher cell concentrations are obtained.

11 Claims, No Drawings

PREPARATION OF CULTURE CONCENTRATES FOR DIRECT VAT SET CHEESE PRODUCTION

BACKGROUND AND PRIOR ART

The manufacture of cheese, yogurt, buttermilk, and similar dairy products requires the use of beneficial lactic acid-producing bacteria. In one procedure which has been in use for many years, the initial cultures are obtained from a culture laboratory, which may be a laboratory engaged in the business of selling cultures to the dairy industry or a laboratory maintained by the cheese manufacturer. These cultures are then used to prepare bulk starter cultures, which are then used to inoculate the milk in the cheese vats. Typical concentrations of such initial cultures have been about $2 \times 10^9$ to 8 CFU (Colony Forming Units) per gram. The direct addition of such initial cultures to the milk in the cheese vats would result in an inefficient process, unless vary large volumes of such culture were used. Although the intermediate step of preparing the bulk starter culture ads to the expense of the operation of the cheese plant, it has been necessary in keeping the production cycle in the cheese vats to a minimum time.

In recent years, culture laboratories have begun to supply culture concentrates which can be used for direct inoculation of the milk in the cheese vats without the necessity of preparing a bulk starter. This process is referred to as the Direct Vat Set or DVS process. For DVS use, it is desirable to have the bacterial cultures as concentrated as possible. Centrifugation is used as the standard means of concentration. With the centrifugal apparatus commonly employed for this purpose, the aqueous liquid is discharged from the centrifuge and the bacteria collect on the bowl of the centrifuge from whence they may be scraped out or mechanically ejected during the operation of the centrifuge. Since the fermented culture contains residual nutrients some of which are in the form of undissolved solid particles, it is not always possible to make a clean separation of the bacterial cells from the medium and residual nutrients. Some cells are lost with the discharge liquid, and part of the residual nutrients are retained with the recovered cells. The theoretical objective, of course, is to recover 100% of the cells completely free of media constituents which, while not harmful, limit the obtainable cell concentration per unit volume. There has, therefore, been a search for means to improve the cleanness of the cell separation without sacrificing cell recovery particuarly when milk and/or whey constitute the growth media.

It has been found that somewhat higher cell concentrations can be produced when citrate ions are present in the media during the centrifugation. Sodium citrate is the reagent which has been used primarily for this purpose. However, the obtainable concentrations have still not been as great as desirable, and when sufficient citrate is present to promote the separation of the cells, it may have an adverse effect on the activity of the culture. Another procedure which has been used to some extent is the addition of a proteolytic enzyme to the fermented culture as described in U.S. Pat. No. 2,838,443. The enzyme treatment is of particular value in improving the cleanness of the cell separation when milk protein (casein) is present in the media.

With either citrate or enzyme, it has been difficult to regularly obtain with most mixed strain lactic streptococcus cultures cell concentrates containing as much as $50 \times 10^9$ CFU per gram. However, concentrations of $100 \times 10^9$ CFU per gram or higher would be desirable for DVS, especially if these can be obtained without reducing cell recovery.

SUMMARY OF INVENTION

This invention is based in part on the discovery that a polyphosphate, such as sodium hexametaphosphate (SHMP), effectively promotes the recovery and concentration of bacterial cells from fermentation media. The mechanism of action of the polyphosphate is not known with certainty. It is believed to act as a dispersant for the residual solids of the media, such as residual casein. Since the media constituents are conventionally formulated from non-fat dry milk solids, sweet whey solids, or both, they will normally contain considerable amounts of residual casein, and whey protein both of which may be in a denatured form. In the separation of the cells by centrifugation, some of the residual casein and whey protein may be trapped in the cell mass, thereby reducing the concentration of the centrifuged cells. By acting to disperse these proteins, more of same may be separated with the liquid and less retained with the cells. However, this theory does not completely explain the action of the polyphosphate. In connection with the development of the present invention, it has been demonstrated experimentally that not only can higher concentrations of cells be obtained but also increased cell recovery is effected. This may, in part, be related to alterations in the electrostatic charges on the cells and/or media substituents. However, a proven theoretical explanation is not available.

Under commercial operating conditions, it has been found possible to recover 98-100% of the cells while achieving concentrations in excess of $50 \times 10^9$ CFU per gram. Typical production run concentrations for producing direct vat set cheese cultures are in the range of $80 \times 10^9$ to $200 \times 10^9$ CFU per gram. Under some conditions, even higher concentrations can be obtained up to $400 \times 10^9$ CFU per gram.

Although phosphates have been present in culture media used for growing cheese starters in cheese factories, they have been present for other purposes than that of the present invention, and, as far as is known, the resulting fermented cultures have not been subjected to centrifugation. As far as we are aware, the value of polyphosphate in promoting the centrifugal separation and recovery of bacterial cells has not been previously recognized or reported. As described in U.S. Pat. Nos. 3,041,248 and 3,354,049 the presence of phosphates in a bacterial culture media may be desirable to control bacteriophage. While both orthophosphates and pyrophosphates have been suggested for this purpose, it is believed that in commercial practice orthophosphates have been used rather than pyrophosphates, or other polyphosphates. Orthophosphates are not suitable for the purpose of the present invention. In some commercial fermentation media sold for use in preparing bulk starter cultures, sodium hexametaphosphate is present with sodium citrate. However, bulk starter cultures are not centrifuged, but rather are charged to the cheese vats as produced.

DETAILED DESCRIPTION

The method of this invention may be used for preparing concentrated bacterial cultures from beneficial lactic acid-producing bacteria, such as those employed for preparing cheese, yogurt, buttermilk, etc. The method will be particularly applicable to the processing of bacterial cultures for use in direct vat set cheese production, wherein the batches of milk are inoculated directly with the culture concentrates. Among the lactic acid-producing bacteria which can be processed by the method of the present invention are the following: *Streptococcus lactis, Streptococcus cremoris, Streptococcus diacetylactis, Streptococcus thermophilus, Lactobacillus bulgaricus, Lactobacillus acidophilus, Lactobacillus helveticus, Lactobacillus bifidus, Lactobacillus casei, Lactobacillus lactis, Lactobacillus plantarum, Lactobacillus delbrueckii, Lactobacillus thermophilus, Lactobacillus fermetii, Pediococcus cervisiae* and *Leuconostoc cremoris*.

The method may also be used for processing mixed strains of the same bactrial species. Since the use of multiple strains of the same bacterial species is desirable in starter cultures, it is advantageous that the centrifugation in the presence of polyphosphate does not significantly affect the relative proportions of the strains in the concentrated product. The same consideration applies to the culturing and concentration of mixed species, such as mixed cultures of *S. thermophilus* and *L. bulgaricus*, as desired for production of Mozzarella and other Italian type cheeses. It is therefore unnecessary to separately culture each strain or species, and then mix the strains or species after concentration, as described in U.S. Pat. No. 3,420,742. The aqueous fermentation media used for culturing the bacteria will be the same as those previously employed for that purpose. The media will ordinarily contain milk proteins, added either as non-fat dry milk solids, or sweet whey solids, or both. The media will also contain fermentable carbohydrates such as lactose and glucose. It may also contain growth stimulants, inorganic salts, buffers, etc. The fermentation nutrients of the media may be and usually are present both as dissolved nutrients and dispersed solid particles. On a total solids basis, the media will usually contain from 4 to 12% nutrients. Where at least 1% of the nutrients are provided by non-fat dry milk solids, the method of this invention is particularly advantageous, although not limited to such media.

If desired, the polyphosphonate can be incorporated in the media prior to the fermentation. This may be of advantage where it is important to control bacteriophage. However, the amount of polyphosphate present during the fermentation should not be so great as to inhibit the growth of the bacteria. Fortunately, the benefit of the polyphosphate in the centrifugal concentration following fermentation can be obtained at a polyphosphate level, such as 1% based on the weight of the media, at which the polyphosphate can also be of value in controlling phage. If desired, additional phosphate can be added to the media in the form of orthophosphate to serve as a buffer. The orthophosphate, however, has little value in promoting the centrifugal separation.

In practicing the present invention, the important consideration is to have the polyphosphate present as a dissolved constituent of the aqueous medium during the centrifugal recovery of the cells. Some or all of the polyphosphate can therefore be added on completion of the fermentation. Based on the weight of the fermented aqueous culture (medium and cells), from 0.25 to 5.0% of the polyphosphate can be present during the centrifugation. The polyphosphate is used in the form of a food-acceptable water-soluble salt, such as the sodium, potassium, or ammonium salt. There is no criticality to the particular salt providing the salt is food-acceptable. A preferred polyphosphate is referred to commercially as "hexametaphosphate", although it is not a specific compound but rather a mixture of polyphosphates, which may contain from 4 to 22 phosphate groups per molecule. Hexametaphosphate is usually supplied as a sodium salt and can be advantageously used in this form for the purpose of the present invention. Hexametaphosphate containing from 6 to 21 phosphate groups per molecule is particularly desirable. Such glassy phosphates are supplied by a number of companies, such as the glassy phosphates sold by FMC Corporation, New York, N.Y., under the trademark names of "Hexaphos" and "Sodophos". Tripolyphosphate can also be used.

An advantageous level of the polyphosphate salt during centrifugation is from about 0.5 to 4.0% based on the weight of the fermented culture being processed (cells and medium). However, higher and lower concentrations can be used while still obtaining some of the benefits of the present invention. For promoting the separation, the concentration should be at least 0.25% based on the culture being processed. At very high concentrations, such as those above 6.0%, there may be an adverse effect on the activity of the cells. Consequently, even when the polyphosphate is added following the fermentation and the contact time with the cells is relatively short, it will usually not be advantageous to employ more than 5.0% of the polyphosphate salt. The polyphosphate salt is dissolved in the aqueous media, and therefore it is in intimate contact with the residual solids of the fermentation as well as with the cells. This is all that is required to obtain the benefits of the present invention. The centrifugation step itself is carried out in the same manner as previously using standard centrifuges of the kind employed for concentrating bacterial cells. By having the polyphosphate salt present, significantly greater concentrations of the cells per unit volume can be obtained. Also in most embodiments, total cell recovery will also be improved. Substantially complete recoveries of the cells are possible, such as recoveries of 98–100% of the cells. Further, the cell concentrates will preferably contain in excess of $50 \times 10^9$ CFU per gram. Particularly advantageous concentrates will contain at least $80 \times 10^9$ CFU, such as concentrates in the range of $80 \times 10^9$ to $200 \times 10^9$ CFU per gram.

This invention in its theoretical and commercial aspects can be better understood from the following experimental and commercial examples.

EXPERIMENTAL EXAMPLES

For comparative purposes, a series of tests were carried out in 2 liter flasks. The procedure was as follows:

A mixed strain lactic culture containing *Streptococcus lactis* and *Streptococcus cremoris* (Chr. Hansen's Laboratory, Inc., Milwaukee, Wis., culture #44) was inoculated at 1.0% into 2 liter aliquots of pasteurized (90° C for 60 minutes) medium at 22° C. The various media formulations are set out in the tables of data. The inoculated medium was then incubated for 16 hours at 22° C. After 16 hours of incubation the cultured medium was cooled to 7° C and the pH was adjusted to 6.0 with concentrated $NH_4OH$. The time and % of addition of polyphosphate is set out in the tables. Adequate mixing was employed during polyphosphate addition. 230 ml samples were then centrifuged on a SORVAL RC-2B laboratory centrifuge at $8,000 \times G$ for 30 minutes at 7°–10° C. Supernatant fractions were carefully decanted and the weights of the cell/medium concentrates were determined. These concentrates were then plated in triplicate on Ellikers lactic agar at dilutions of $10^8$–$10^{10}$.

The plates were incubated at 30° C for 3 days. All colonies were counted and these counts are reported in terms of colony forming units (CFU) per gram. Since the chain length varies in lactic streptococci as a function of strain, growth media constituents, fermenter agitation, growth temperature, etc., the individual colonies may represent anywhere from 1-30 bacterial cells or more. Thus, the need for the designation as colony forming units (CFU). Since centrifugation disrupts (reduces) chain length it is difficult to precisely ascess the % of cell recovery in some cases.

The test used a variety of media, all formulated to 9% total solids in water. Controls were run with no polyphosphate addition, and the same media were separately tested with the addition of sodium hexametaphosphate at a 2% level with addition before and after fermentation. The SHMP was "Hexaphos", obtained from FMC Corporation, New York, N.Y. It is specified as containing an average of approximately 13 phosphate groups per molecule.

The data obtained are set out below in Tables A, B, C and D.

TABLE A

| | (Control - No Polyphosphate) | | |
|---|---|---|---|
| FORMULA* | CULTURE CFU** at $10^7$/gram | CONC CFU × $10^9$/gram | CONC. WT. (grams) |
| I All NFS (non-fat dry milk solids) | 46.6 | 10.2 | 11 |
| II All Sweet Whey Solids*** | 44.6 | 32.6 | 7.8 |
| III All Whey Protein Concentrate Solids**** | 52.6 | 10.6 | 14.2 |
| IV 50/50 NFS + Sweet Whey Solids | 47.0 | 9.6 | 15.2 |
| V 50/50 NFS + Whey Protein Concentrate Solids | 46.0 | 9.2 | 13.0 |
| VI 50/50 Sweet Whey Solids + Whey Protein Concentrate Solids | 55.3 | 9.4 | 16.7 |

*Formula: 6% total of listed ingredients (NFS, Sweet Whey, etc.) + 1% glucose, +1% yeast extract paste + 0.75% Diammonium Phosphate (DAP) & 0.25% Monoammonium Phosphate (MAP).
**Colony Forming Units determined by standard plate count method, as described above.
***Krafen from Kraftco.
****Puritein 29 from Purity Cheese Co.

TABLE B

| | (2% SHMP*Added Before Growth) | | |
|---|---|---|---|
| FORMULA** | CULTURE CFU*** at $10^7$/gram | CONC. CFU × $10^9$ gram | CONC. WT. (grams) |
| I NFS (non-fat dry milk solids) | 60 | 55.2 | 4 |
| II Sweet Whey Solids | 8.33 | 18 | 7 |
| III Whey Protein Concentrate Solids | 67.3 | 28.8 | 7 |
| IV 50/50 NFS + Sweet Whey Solids | 51.7 | 61.8 | 6 |
| V 50/50 NFS + Whey Protein Concentrate Solids | 69.7 | 33 | 6 |
| VI 50/50 Sweet Whey Solids + Whey Protein Concentrate Solids | 44.0 | 64.6 | 6.2 |

*Sodium hexametaphosphate.
**Formula: 6% total of listed ingredients + 1% glucose + 1% yeast extract paste + 0.75% DAP & 0.25% MAP.
***Colony Forming Units.

TABLE C

| | (2% SHMP*Added After Growth) | | |
|---|---|---|---|
| FORMULA** | CULTURE CFU*** at $10^7$/gram | CONC. CFU × $10^9$/gram | CONC. WT. (grams) |
| I All NFS | 46.6 | 80.6 | 3 |
| II All Sweet Whey Solids | 44.6 | 37.6 | 6.7 |
| III All Whey Protein Concentrate Solids | 52.6 | 49.8 | 3.0 |
| IV 50/50 NFS + Sweet Whey Solids | 47.0 | 26.4 | 8.2 |
| V 50/50 NFS + Whey Protein Concentrate Solids | 46.0 | 55.8 | 2.5 |
| VI 50/50 Sweet Whey Solids + Whey Protein Concentrate Solids | 55.3 | 32.2 | 7.0 |

*Sodium hexametaphosphate.
**Formula: 6% total of listed ingredients + 1% glucose + 1% yeast extract paste + 0.75% DAP & 0.25% MAP.
***Colony Forming Units.

TABLE D

| | (Comparative Summary) | | |
|---|---|---|---|
| | CONCENTRATION $\frac{CFU \times 10^9}{gram}$ | | |
| FORMULA | Control | 2% SHMP Before Growth | 2% SHMP After Growth |
| I (Milk) | 10.2 | 55.2 | 80.6 |
| II (Whey) | 32.6 | 18 | 37.6 |
| III (Whey Protein Conc.-"WPC") | 10.6 | 28.8 | 49.8 |
| IV (Milk and Whey) | 9.6 | 61.8 | 26.4 |
| V (Milk and WPC) | 9.2 | 33 | 55.8 |
| VI (Whey and WPC) | 9.4 | 64.6 | 32.2 |

The foregoing data should be considered on a comparative rather than an absolute basis. The concentrations of bacteria at the conclusion of the fermentation are considerably lower than those obtained in commercial practice, using large fermenters equipped with agitators and pH control equipment. The final cell concentrations obtained in commercial practice will therefore be considerably higher than those reflected by the above data. However, the data is valid as showing relative concentrations, and improved concentrations of the same order proportionately can be expected in commercial practice. In commercial runs using the method of this invention, bacterial concentrates are obtained containing in excess of $50 \times 10^9$ CFU, and typically the concentrates produced by the method of this invention for direct vat set cheese making contain about $80 \times 10^9$ to $200 \times 10^9$ CFU per gram. Further, substantially complete recoveries of the bacteria cells are obtained, such as recoveries of about 98% or better.

The details of such commercial embodiments are further illustrated by the following examples.

COMMERCIAL EXAMPLES

EXAMPLE 1

450 gallons of medium containing 6% by weight NFS milk solids, 1% glucose and 1% yeast extract is charged into a 500 gallon capacity dairy processor. The medium is subsequently pasteurized at 90° C for 60 minutes under constant agitation at 24 RPM after which the medium is brought to 26°–30° C. The medium is then inoculated at 2% by volume with an active mixed strain subculture of *Streptococcus lactis* plus *Streptococcus cremoris* (Chr. Hansen's - culture #840).

The inoculated medium is then incubated for 10–12 hours at 26°–30° C with constant agitation at 24 RPM and automatic pH control at pH 5.80 to 6.20. Concentrated ammonium hydroxide is used for pH neutralization. After 10–12 hours of incubation and pH control the pH is adjusted to 6.40–6.80 with simultaneous cooling to 12°–16° and simultaneous addition of 2% by weight sodium hexametaphosphate (FMC-hexaphos). Agitation is increased to 48 RPM to effect dissolution of the SHMP. After 30–60 minutes of mixing the cooled cultured medium is centrifuged on an automatic desludging CIP separator. The culture at 15° is fed at 600 gallons per hour to the separator. The automatic desludging is adjusted to give a 5% by volume yield of concentrated based upon the total feed volume. The expelled supernatant waste contains less than 1% of the total bacteria processed. The concentrate prepared is 20 times the strength of the feed culture.

Typical values for culture concentrates of #840 in terms of CFU on Ellikers lactic agar range from $150 \times 10^9$ to $250 \times 10^9$ CFU per gram. 360 ml of such concentrate provides sufficient inoculum for the direct vat inoculation of 5000 pounds of milk for cheddar cheese. Such concentrates are typically frozen in liquid nitrogen at −196° C in aluminum cans and are made commercially available in this form.

EXAMPLE 2

450 gallons of medium similar to that in Example 1 only with ½ of the total NFS milk solids replaced with sweet whey solids is charged into a 500 gallon dairy processor. 1% by weight sodium hexametaphosphate (FMC-hexaphos) is added with constant agitation prior to pasteurization. Chr. Hansen's Laboratory, Inc. culture #630 is used as the inoculum. This culture contains two separate strains of *Streptococcus lactis*.

The basic procedure is then that of Example 1 except that no SHMP is added after fermentation. The centrifuged cell concentrates from culture #630 have typical CFU values of $250 \times 10^9$ to $350 \times 10^9$ per gram when discharged from the separator at 5% of the total initial volume. 360 ml of this concentrate is sufficient inoculum for 10,000 pounds of milk for cheddar cheese manufacturing.

EXAMPLE 3

The procedure of Example 1 is followed exactly except that instead of using sodium hexametaphosphate the reagent used is 3% sodium tripolyphosphate. CFU values of the resultant centrifuged cell concentrate range from $100 \times 10^9$ to $150 \times 10^9$ CFU per gram. Cells are discharged at 5% of total fermenter volume.

EXAMPLE 4

The modified procedure of Example 3 is followed except that 4% sodium pyrophosphate is employed instead of 3% sodium tripolyphosphate. CFU values range from $100-150 \times 10^9$ per gram.

EXAMPLE 5

200 gallons of media containing 4% sweet whey solids by weight, 2% NFS milk solids, 1% yeast extract, 1% sodium citrate, and various mineral salts of potassium, manganese and magnesium is charged into a 200 gallon dairy processor. The media is pasteurized and subsequently tempered to 22°–26° C. Inoculation follows at 2% by volume with a skim milk subculture of *Leuconostoc cremoris* (CHL Strain CAF-1). Incubation is then commenced at 22°–26° C for 20–24 hours with automatic pH control at pH 5.80–6.20 using concentrated ammonium hydroxide as the neutralizing agent. After 20–24 hours of said incubation the 200 gallons of culture is cooled to 12°–16° C with the simultaneous addition of 4% by weight sodium hexametaphosphate (Monsanto-food grade). Adequate agitation at 48 RPM is effected for 30 minutes. Said culture is then separated at $14,000 \times G$ on a Carl Padberg Model Z-101 super centrifuge. The resultant cell concentrate is adjusted to 6% of the total initial culture volume with sterile skim milk. Said concentrate contains $50 \times 10^9$ to $60 \times 10^9$ CFU per gram when assayed on Nickels calcium citrate agar. Such a concentrate of *Leuconostoc cremoris* is used to augment the *Streptococcus lactis/cremoris* concentrates in the manufacturing of certain varieties of cheese.

EXAMPLE 6

The procedure of Example 2 is followed with the following exceptions: 1% NFS milk powder and 5% sweet whey powder combined with 1% glucose and 1% yeast extract constitute the medium formulation. A single strain of *Streptococcus diacetylactis* (Chr. Hansen's Strain AFI-1) cultured in sterile skim milk is used to inoculate the medium. Resulting concentrates of AFI-1 range from $100 \times 10^9$ to $125 \times 10^9$ CFU per gram when discharged at 6% of the total volume centrifuged.

We claim:

1. The method of preparing concentrated bacterial cultures for direct vat inoculation of milk batches in which harmless lactic acid-producing bacteria are cultured in an aqueous medium including fermentation nutrients to obtain a fermented aqueous culture of the bacteria cells together with residual nutrients including casein, wherein the improvement comprises recovering and concentrating said cells by subjecting said culture to centrifugation while having dissolved therein from 0.25 to 5.0% based on the weight of the culture of water-soluble food-acceptable polyphosphate salt selected from the class consisting of tripolyphosphate and hexametaphosphate containing from 4 to 22 phosphate groups per molecule, said centrifugation producing a cell concentrate of said bacteria having in excess of 50 × $10^9$ CFU per gram.

2. The method improvement of claim 1 in which said polyphosphate salt is present during said centrifugation in an amount of from 0.5 to 4.0% based on the weight of said fermented culture.

3. The method improvement of claim 1 in which said polyphosphate salt is sodium hexametaphosphate.

4. The method improvement of claim 1 in which said polyphosphate salt is sodium tripolyphosphate.

5. The method of preparing concentrated bacterial cultures for direct vat inoculation of milk batches in which harmless lactic acid-producing bacteria are cultured in an aqueous medium including fermentation nutrients to obtain a fermented aqueous culture of the bacteria cells together with residual nutrients including casein, wherein the improvement comprises recovering and concentrating said cells by subjecting said culture to centrifugation while having dissolved therein from 0.5 to 4.0% based on the weight of the culture of a water-soluble food-acceptable phosphate salt selected from the class consisting of tripolyphosphate and hexametaphosphate containing from 4 to 22 phosphate groups per molecule, said centrifugation producing a cell concentrate of said bacteria having at least 100 × $10^9$ CFU per gram.

6. The method improvement of claim 5 in which said aqueous medium at the start of said fermentation contains from 4 to 12% of said nutrients based on the weight of the medium and at least 1% of said nutrients on a dry solids basis is provided by non-fat dry milk solids.

7. The method of preparing concentrated bacterial cultures for direct vat inoculation of milk batches in which harmless lactic acid-producing bacteria are cultured in an aqueous medium including fermentation nutrients to obtain a fermented aqueous culture of the bacteria cells together with residual nutrients including casein, wherein the improvement comprises recovering and concentrating said cells by subjecting said culture to centrifugation while having dissolved therein from 0.5 to 4.0% based on the weight of the culture of sodium hexametaphosphate containing from 6 to 21 phosphate groups per molecule, said centrifugation producing a cell concentrate of said bacteria having at least 100 × $10^9$ CFU per gram.

8. The method improvement of claim 7 in which said aqueous medium at the start of said fermentation contains from 4 to 12% of said nutrients based on the weight of the medium and at least 1% of said nutrients on a dry solids basis is provided by non-fat dry milk solids.

9. The method of preparing concentrated bacterial cultures for direct vat inoculation of milk batches in which harmelss lactic acid-producing bacteria are cultured in an aqueous medium including fermentation nutrients to obtain a fermented aqueous culture of the bacteria cells together with residual nutrients including casein, wherein the improvement comprises recovering and concentrating said cells by subjecting said culture to centrifugation while having dissolved therein from 0.5 to 4.0% based on the weight of the culture of sodium hexametaphosphate, said centrifugation producing a cell concentrate of said bacteria having from 150 × $10^9$ to 250 × $10^9$ CFU per gram.

10. The method improvement of claim 9 in which said aqueous medium at the start of said fermentation contains from 4 to 12% of said nutrients based on the weight of the medium and at least 1% of said nutrients on a dry solids basis is provided by non-fat dry milk solids.

11. The method of preparing concentrated bacterial culture for direct vat inoculation of milk batches in which harmless lactic acid-producing bacteria are cultured in an aqueous medium including fermentation nutrients to obtain a fermented aqueous culture of the bacteria cells together with residual nutrients, said aqueous medium at the start of said fermentation containing from 4 to 12% of said nutrients based on the weight of the medium and at least 1% of said nutrients on a dry solids basis being provided by non-fat dry milk solids, wherein the improvement comprises recovering and concentrating said cells by subjecting said culture to centrifugation while having dissolved therein from 0.5 to 4.0% based on the weight of the culture of water-soluble food-acceptable polyphosphate salt selected from the class consisting of tripolyphosphate and hexametaphosphate containing from 4 to 22 phosphate groups per molecule, said centrifugation producing a cell concentrate of said bacteria having in excess of 100 × $10^9$ CFU per gram.

* * * * *